(12) United States Patent
Takahashi

(10) Patent No.: US 8,128,891 B2
(45) Date of Patent: Mar. 6, 2012

(54) AUTOMATED ANALYZER

(75) Inventor: Katsuaki Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 262 days.

(21) Appl. No.: 12/200,387

(22) Filed: Aug. 28, 2008

(65) Prior Publication Data

US 2009/0060784 A1 Mar. 5, 2009

(30) Foreign Application Priority Data

Aug. 31, 2007 (JP) ................................. 2007-224995

(51) Int. Cl.
*B01L 3/00* (2006.01)
(52) U.S. Cl. ............ 422/500; 422/501; 436/180; 73/304
(58) Field of Classification Search ............ 422/99–100, 422/500–501; 436/180; 73/304
See application file for complete search history.

(56) References Cited

U.S. PATENT DOCUMENTS

| 3,739,821 A * | 6/1973 | Watkin et al. ............... 73/864.24 |
| 4,287,155 A * | 9/1981 | Tersteeg et al. ................. 422/64 |
| 4,574,850 A | 3/1986 | Davis |
| 4,818,492 A * | 4/1989 | Shimizu ........................ 422/509 |
| 5,550,059 A * | 8/1996 | Boger et al. .................... 436/54 |
| 6,379,624 B1 | 4/2002 | Lange |
| 2003/0087442 A1 | 5/2003 | Popa-Burke et al. |
| 2004/0096368 A1 | 5/2004 | Davis et al. |

FOREIGN PATENT DOCUMENTS

| JP | 61-169736 A | 7/1986 |
| JP | 5-164764 | 6/1993 |
| JP | 6-242126 | 9/1994 |
| JP | 8-122126 A | 5/1996 |
| JP | 2001-504212 A | 3/2001 |

* cited by examiner

*Primary Examiner* — Jyoti Nagpaul
(74) *Attorney, Agent, or Firm* — Mattingly & Malur, PC

(57) ABSTRACT

An automated analyzer includes pipetting means for discharging a sample and reagent into an empty reaction vessel without causing contact to occur between the leading end of a sample probe and the bottom of the reaction vessel. The sample probe is inserted into the reaction vessel and then stopped when a bottom end of an outer pipe of the sample probe comes in contact with the top edge of the reaction vessel to maintain a fixed gap between the leading end of an inner pipe of the sample probe and the bottom of the reaction vessel. Further, an insulating material is disposed between the inner and outer pipes of the sample probe.

3 Claims, 4 Drawing Sheets

AUTOMATED ANALYZER

BACKGROUND OF THE INVENTION

1. Field of the Invention

The present invention relates to an automated analyzer which automatically analyzes components of biological samples such as blood, urine, etc. More particularly, the present invention relates to an automated analyzer which collects a liquid from a sample vessel and a reagent vessel and discharges it into a reaction vessel.

2. Description of the Related Art

With automated analyzers, methods for discharging a sample into a reaction vessel are roughly classified into the following two types. A first method is a technique in which the leading end of a sample probe is brought into contact with the bottom of an empty reaction vessel and then the sample is discharged. A second method is a technique in which a reagent is pipetted first, the leading end of the sample probe is brought into contact with the reagent, and the sample is discharged into the reagent. In recent years, the amount of reaction liquid as well as the amount of reagent used per analysis have been reduced in terms of reduction in running cost, and accordingly the amount of a sample to be pipetted has been reduced to a minute amount. Further, in order to improve the throughput, measures for increasing the analysis speed has been actively taken. In particular, an increase in pipetting speed is also a very important factor. However, these conventional methods have the following drawbacks.

With the first method, the leading end of the sample probe or the bottom of the reaction vessel is damaged, resulting in degradation of the pipetting accuracy in many cases. Recently, the leading end of the sample probe is made thin and sharp in order to maintain the pipetting accuracy with a minute amount of sample pipetted, that is, 1 microliter or less, which makes the bottom of the reaction vessel and the leading end of the sample probe susceptible to damage. With the second method, it is necessary to clean the inside and outside of the sample probe for each pipetting because the leading end of the sample probe comes in contact with the reagent. The second method has drawbacks that the necessity to perform cleaning process in each cycle (for each analysis item) may impair the improvement in throughput and that a large amount of cleaning water is required. With the first method, it is only necessary to clean the inside and outside of the sample probe only when the sample is changed. JP-A-5-164764 discloses a compromise method as an improved version of the two methods. This method first discharges the reagent into the reaction vessel, and performs very severe control so as to stop the sample probe at the moment when the drop of the discharged sample liquid at the leading end of the sample probe almost comes in contact with the reagent. JP-A-6-242126 discloses a pipetting method that takes damage to the probe into consideration.

SUMMARY OF THE INVENTION

The technique described in JP-A-5-164764 has low practicability because of fluctuations in surface meniscus (curved liquid surface caused by wettability) of a reagent, fluctuations of the height of a reaction vessel, fluctuations of the section area of the reaction vessel, and the like. Further, if a sample probe is inserted into the sample while the reagent adheres to the leading end of the sample probe (without cleaning), there is a risk of contaminating the sample with the reagent.

Further, the technique described in JP-A-6-242126 does not take into consideration at all fluctuations of the bottom height of the reaction vessel. When a small amount of sample is pipetted, the gap between the leading end of the sample probe and the bottom of the reaction vessel is substantially zero, that is, the leading end of the sample probe and the bottom of the reaction vessel do or do not come in contact with each other depending on fluctuations of the height of the reaction vessel, which may contrarily degrade the pipetting accuracy.

An object of the present invention is to provide an automated analyzer which can maintain the pipetting accuracy without damaging the leading end of the sample probe and the bottom of the reaction vessel, even if a minute amount of sample is pipetted, even in a case where the sample is discharged into an empty reaction vessel with the first method.

In order to attain the above-mentioned object, the present invention is configured as follows.

An automated analyzer comprises: a sample pipetting probe; a reaction vessel; and a stepped portion provided on the sample pipetting probe; wherein, when a sample is pipetted into the reaction vessel using the sample pipetting probe, the stepped portion is in contact with the reaction vessel and restricts the amount of lowering of the pipetting probe toward the reaction vessel to a predetermined amount. The stepped portion may have any desired shape as long as it limits the operation of the pipetting probe so that the pipetting probe is not lowered any more when the stepped portion abuts with the top surface (top edge) of the reaction vessel. For example, providing a double pipe concentrically with the pipetting probe makes the lower end of the outer pipe serve as the stepped portion. Alternatively, a projection may be provided on the outer side the pipetting probe.

In accordance with the present invention, upon sample pipetting into the reaction vessel, the leading end of the sample probe does not come in contact with the bottom of the reaction vessel, preventing the probe and reaction vessel from being damaged. Accordingly, a fixed gap can be maintained between the leading end of the sample probe and the bottom of the reaction vessel, making it possible to improve and maintain the pipetting accuracy. Upon sample pipetting according to the present invention, it is preferable to clean the inside and outside of the sample probe only when the sample is changed, and it is not necessary to clean the sample probe as long as the same sample is pipetted, thus shortening the pipetting cycle and accordingly improving the analysis throughput.

DESCRIPTION OF THE PREFERRED EMBODIMENTS

The present invention is characterized in that, when a sample probe is inserted into an empty reaction vessel for sample pipetting, the leading end of the sample probe is not brought into contact with the bottom of the reaction vessel and a fixed gap (about 0.05 millimeters) is maintained therebetween upon sample discharge. A plurality of reaction vessels are arranged on a reaction disk. It is very difficult to maintain the fixed gap because of fluctuations of the bottom height of the plurality of reaction vessels, in particular, because of fluttering (height undulation) produced when the reaction disk is rotated. The larger the reaction disk, the larger becomes the fluttering. There is another problem of fluctuations of the position at which the sample probe is stopped after lowering operation. The following measures are taken to maintain a fixed gap.

A stepped portion is provided on the outer wall of the sample probe, and the stepped portion abuts with the top edge of the reaction vessel, thus maintaining a fixed gap between the bottom of the reaction vessel and the leading end of the sample probe. If the reaction vessel is securely molded through plastics molding and then managed, the distance between the top edge of the reaction vessel and the bottom thereof can be maintained constant with an error of 0.01 millimeters or less, that is, almost ignored. The distance between the leading end of the sample probe and the stepped portion can be accurately made when the sample probe is manufactured using, for example, a locking device (with an error of 0.01 millimeters or less).

An embodiment of the present invention will be explained below with reference to the accompanying drawings.

Figure 1:
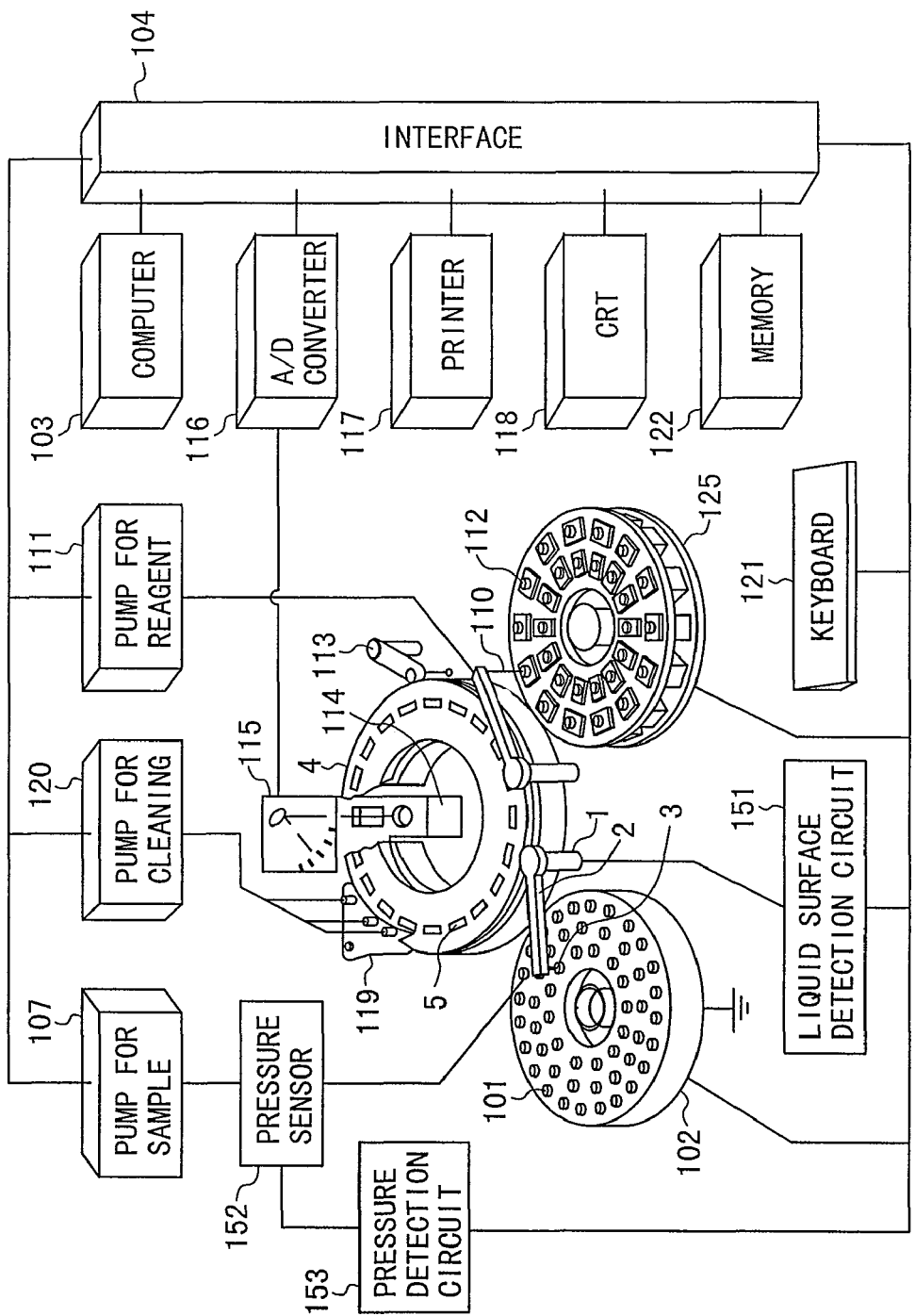
FIG. 1 is a schematic diagram of a general automated analyzer.

FIG. 1 shows the overview of a general automated analyzer according to the present invention.

Since the function of each section is known, detailed description of the function will be omitted. The automated analyzer is configured such that a sampling arm 2 of a sampling mechanism 1 vertically moves and rotates, and a sample probe 3 attached to the sampling arm 2 suctions a sample in a sample vessel 101 installed on a sample disk 102 that rotates clockwise and discharges the sample into a reaction vessel 5. As shown in FIG. 1, the structure of the sample disk 102 is commonly applicable to universal arrangement, that is, the sample vessel 101 is installed directly on the sample disk 102, and the sample vessel 101 can be placed on a test tube (not shown).

A rotatable reagent disk 125 installs thereon reagent bottles 112, each being associated with a plurality of analysis items to be analyzed. A reagent pipetting probe 110 attached to the movable arm pipettes a predetermined amount of reagent from the reagent bottle 112 to the reaction vessel 5.

The sample probe 3 performs sample suction and discharge operations in association with the operation of a syringe pump for sample 107. The reagent pipetting probe 110 performs reagent suction and discharge operations in association with the operation of a syringe pump for reagent 111. Analysis items to be analyzed for each sample are input from an input unit such as a keyboard 121 or the screen of a CRT 118. The operation of each unit in the automated analyzer is controlled by a computer 103.

With the intermittent rotation of the sample disk 102, the sample vessel 101 is transferred to a sample suction position, and the sample pipetting probe 3 is lowered into the sample vessel 101 in a stop. With the lowering operation of the pipetting probe 3, when the tip of the pipetting probe 3 comes in contact with the surface of the sample liquid, a surface detector 151 outputs a detection signal and the computer 103 performs control so as to stop the lowering operation by the drive unit of the sampling arm 2 based on the detection signal. Then, the pipetting probe 3 suctions a predetermined amount of sample and then rises to the upper dead center. While the pipetting probe 3 is suctioning the predetermined amount of sample, a pressure detection circuit 153 monitors pressure fluctuation inside a passage between the pipetting probe 3 and the syringe pump for sample 107 by use of a signal from a pressure sensor 152. If an abnormal pressure fluctuation is detected during suction operation, the predetermined amount of sample may not have been suctioned, and therefore an alarm is added to related analysis data.

Then, the sampling arm 2 horizontally rotates, lowers the sample pipetting probe 3 at the position of the reaction vessel 5 on a reaction disk 4, and the sample pipetting probe 3 discharges the sample into the reaction vessel 5. When the reaction vessel 5 containing the sample is moved to the reagent addition position, a reagent associated with relevant analysis items is added from the reagent pipetting probe 110 into the reaction vessel 5. With the sample and reagent pipetting operations, the liquid surface of the sample in the sample vessel 101 and that of the reagent in the reagent bottle 112 are detected. The mixture of the sample and reagent in the reaction vessel is mixed by a mixer 113. The reaction vessel containing the mixture is transferred to a photometer 115, and the luminescence value or absorbance of each mixture component is measured by a photo-multiplier or photometer as measurement means. A light-emitting signal or light-sensitive signal passes through an A/D converter 116 and then is supplied to the computer 103 through an interface 104 to calculate the concentration that is an analysis item. Analysis results are printed on a printer 117 or displayed on the screen of the CRT 118 and, at the same time, stored in a memory 122 through the interface 104. The reaction vessel 5 that completed photometry is cleaned at the position of a reaction vessel cleaning mechanism 119. The pump for cleaning 120 supplies cleaning water to the reaction vessel while discharging waste water from the reaction vessel. In the example of FIG. 1, three columns of vessel holding sections are formed such that three columns of sample vessels 101 are concentrically set on the sample disk 102, and a sample suction position for the sample pipetting probe 3 is provided for each column.

The general operation of the automated analyzer has been explained above.

While the sample probe repeats the steps of suctioning the sample from the sample vessel, discharging the sample into the reaction vessel, and cleaning the inside and outside of the probe in a sample probe cleaning tub (not shown), the leading end of the sample probe in a conventional automated analyzer comes in contact with the reaction vessel only when the probe discharges the sample into the reaction vessel. If the leading end of the sample probe does not come in contact with the reaction vessel, abrasion or curling of the leading end of the sample probe can be prevented and it possible to semipermanently use the probe as long as the leading end of the probe is not accidentally bent by contact with hand.

For pipetting without contact between the sample probe and the reaction vessel, it is necessary to maintain a fixed gap (about 0.05 mm) between the bottom of the reaction vessel and the leading edge of the sample probe that has been lowered inside the reaction vessel and then stopped.

Figure 3:
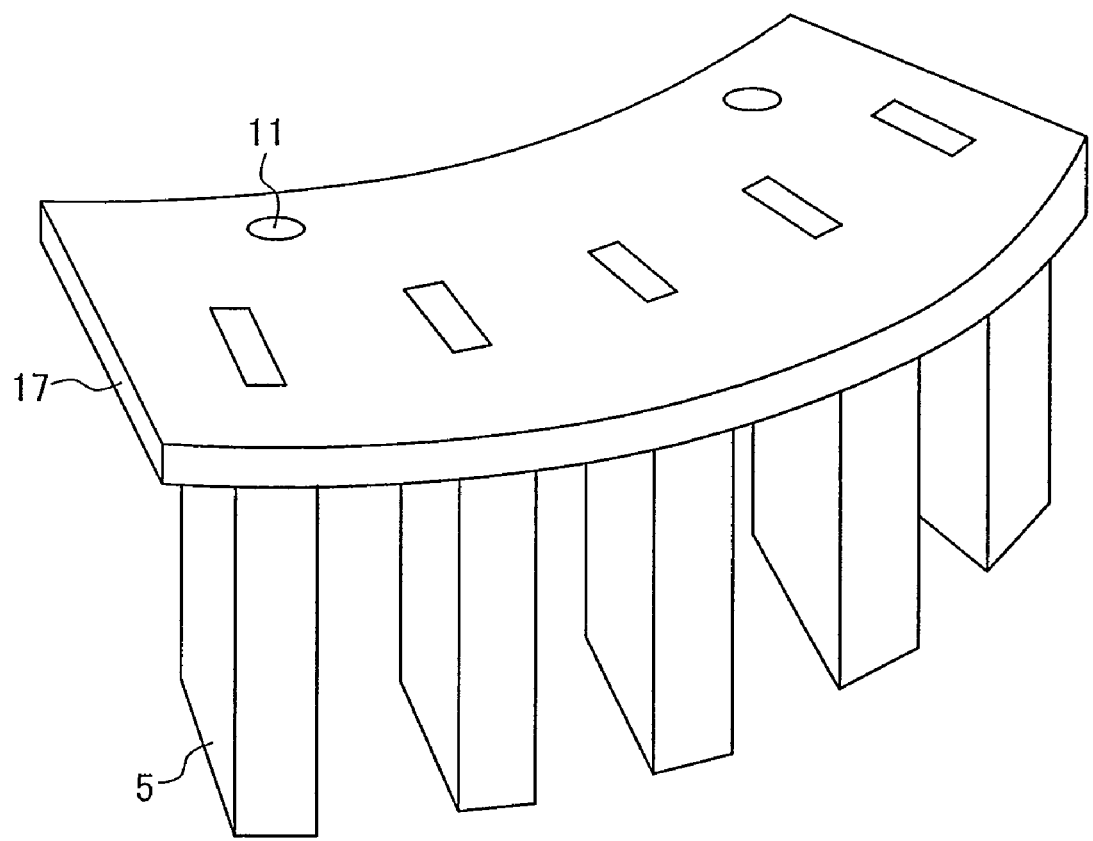
FIG. 3 a diagram showing a split block shaped-reaction vessel.

FIG. 3 diagram showing a split block shaped-reaction vessel. Since it is very difficult to mold the whole circumference of the reaction disk through plastics molding, the whole circumference is composed of a plurality of split blocks, each being shaped as shown in FIG. 3. A reaction vessel block 17 is firmly fixed to the reaction disk 4 using screw holes 11.

Figure 2:
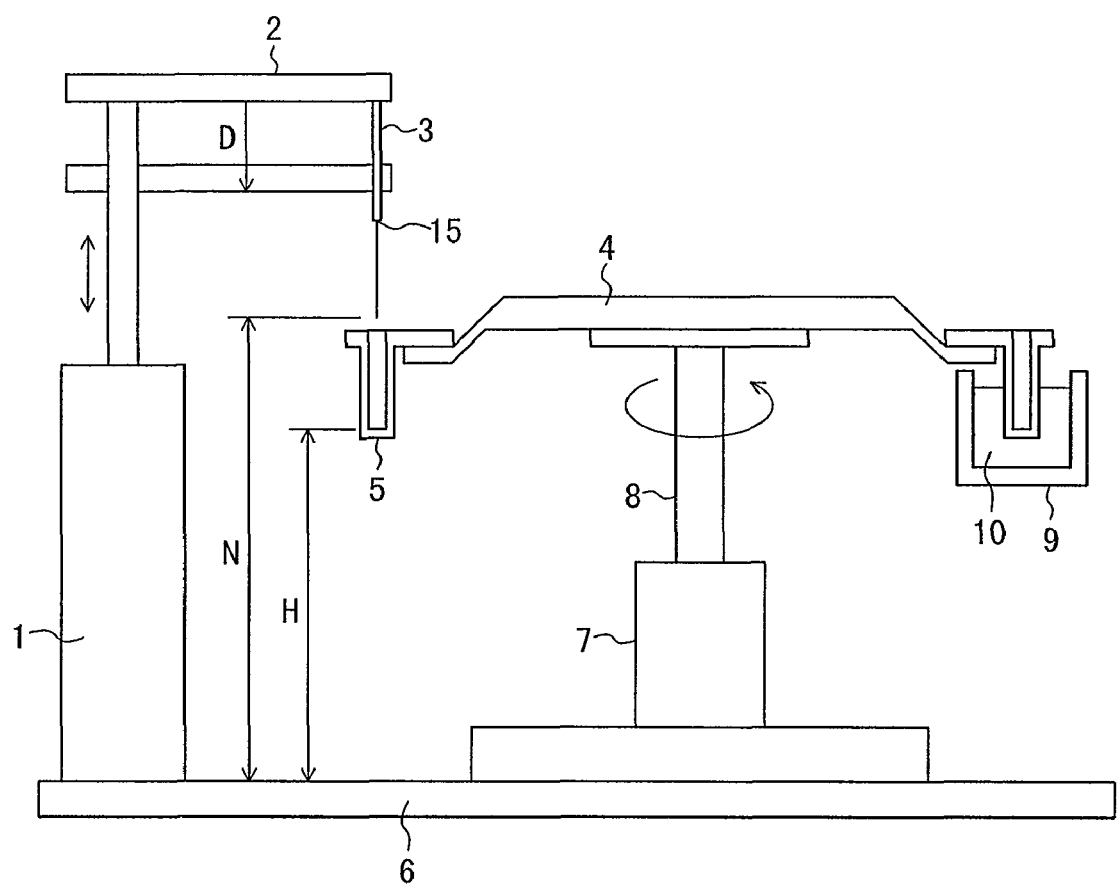
FIG. 2 is a diagram showing a relation between a reaction vessel and the leading end of a sample probe.

FIG. 2 shows a relation between the bottom height of a reaction vessel and the leading end of the sample probe. The reaction disk 4 which installs thereon reaction vessels 5 is driven for rotation by a drive unit 7 and a drive shaft 8 mounted on a mechanism base 6. The height H from the mechanism base to the bottom of the reaction vessel fluctuates for each individual reaction vessel. When the reaction disk is rotated, undulation is inevitably produced. In particular, since the reaction vessel block is molded through resin molding, the undulation is caused mainly by the warpage of the reaction vessel block due to thermally contractive deformation occurring at the time of molding. Further, as shown in FIG. 2, since the reaction vessel is immersed in reaction tub water 10 (37 degrees centigrade) while it is used, water is gradually absorbed into the plastics material of the reaction vessel and accordingly the reaction vessel is warped over time. This warpage is an auxiliary cause of the undulation. Further, the undulation is affected also by the straightness of the drive shaft 8. In this way, the reaction vessel suffer the undulation of the bottom of about 0.3 millimeters. Because of the structure of the sampling mechanism 1, the height of the stop position (N-D) of the sample probe lowered (with an amount of lowering of D) and inserted into the reaction vessel is not necessarily constant owing to backlash (shakiness) of the drive unit which vertically moves and rotates the sample probe 3. The fluctuation of the height of the stop position also is about 0.3 millimeters.

Although the gap can be adjusted to 0.05 millimeters with one reaction vessel, it is clearly difficult to maintain a fixed gap (0.05 millimeters) between the bottom of the reaction vessel and the leading end of the sample probe for all reaction vessels in a state where there are fluctuations of the bottom height of each reaction vessel and the vertical stop position of the sample probe.

Figure 4:
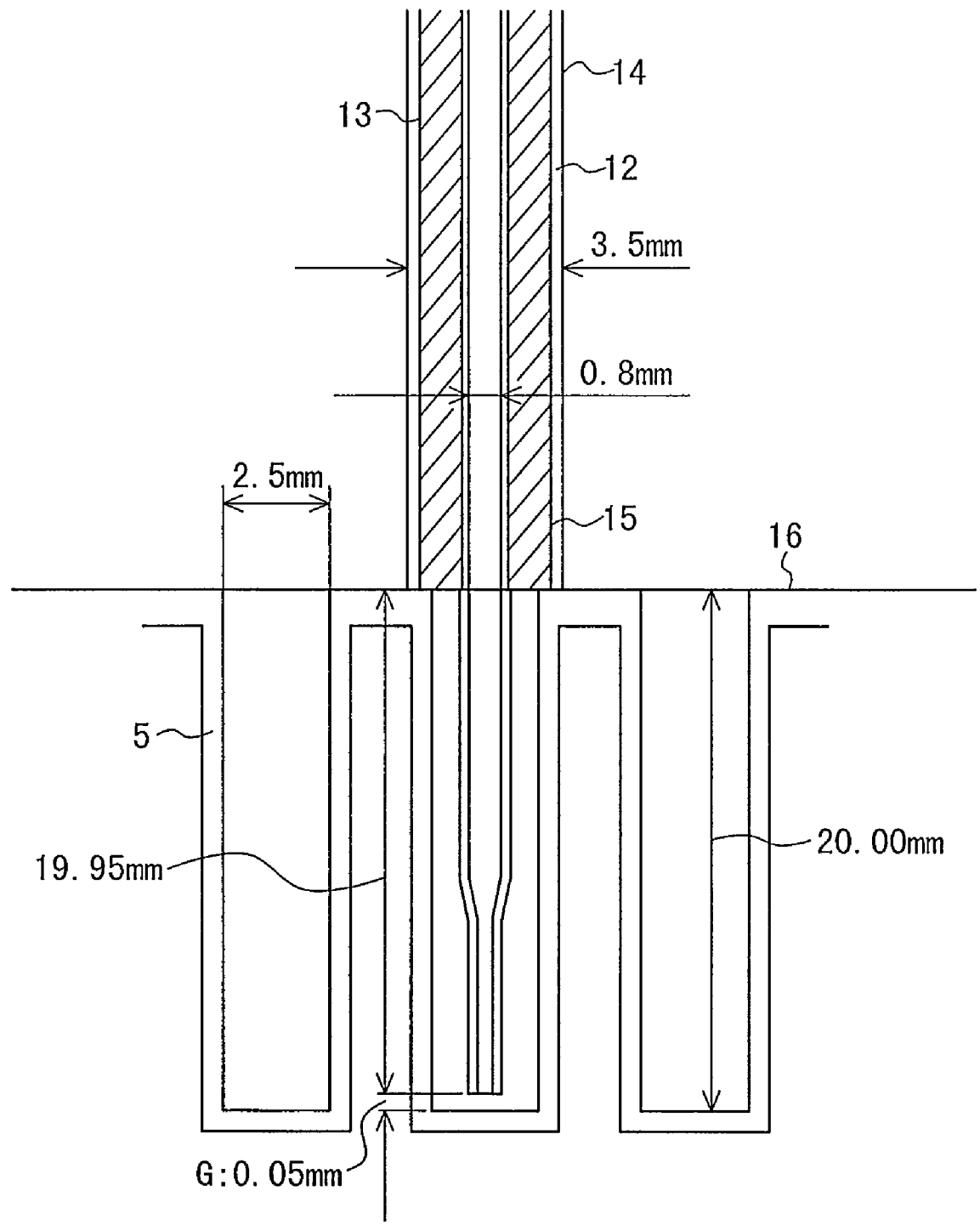
FIG. 4 is a diagram of assistance in explaining a cross-section of a state where the sample probe is inserted into the reaction vessel.

Then, as shown in FIG. 2 or 4, a stepped portion 15 is provided on the outer wall of the sample probe. FIG. 4 shows the structure of the sample probe. The sample probe is of capacitive type and has a double structure. Specifically, the sample probe is composed of a central stainless steel pipe 12 (the main pipe having an outer diameter of 1.1 millimeters and an inner diameter of 0.8 millimeters, and the thinned leading end having an outer diameter of about 0.25 millimeters and an inner diameter of about 0.13 millimeters) for suctioning a sample, an insulating resin 13 surrounding the central stainless steel pipe 12, and a shielding stainless steel pipe 14 bonded to the outside of the insulating resin 13 to shield electric noise. The stepped portion 15 can be formed in such a manner that the shielding stainless steel pipe 14 becomes shorter than the central stainless steel pipe 12. Since the lateral width of the reaction vessel is 2.5 millimeters and the outer diameter of the shielding stainless steel pipe is 3.5 millimeters, the shielding stainless steel pipe does not enter the reaction vessel. Since the distance from the stepped portion to the leading end of the sample probe is 19.95 millimeters and the distance from the top edge of the reaction vessel 16 to the bottom thereof is 20.00 millimeters, the stepped portion of the shielding stainless steel pipe abuts with the top edge of the reaction vessel when the sample probe is inserted into the reaction vessel, thus maintaining a fixed gap of 0.05 millimeters between the leading end of the sample probe and the bottom of the reaction vessel. Naturally, the sampling arm and the sample probe are connected with a spring or the like, allowing the cushioning effects therebetween when the stepped portion abuts with the reaction vessel. An error of this gap may be caused by the fluctuation of depth A of individual reaction vessels (20.00 millimeters in FIG. 4) and an error of accuracy in the distance B between the leading end of the sample probe and the stepped portion. (The distance B may cause an error of accuracy in the gap G (0.05 millimeters) only when the sample probe is replaced with a new one.)

The fluctuation of depth A of individual reaction vessels can be restrained to 0.01 millimeters or less by controlling the manufacturing dimension of a part called core pin (male type) for molding of a reaction vessel. Further, if measurements are taken using an adhesive locking device when the central stainless steel pipe and shielding stainless steel pipe are bonded to each other with insulating resin, the fluctuation of the distance B (19.95 millimeters in FIG. 4) between the leading end of the sample probe and the stepped portion can be infinitely minimized to zero. In this may, the gap G (0.05 millimeters) can be restrained to 0.04 to 0.05 millimeters.

If the sample is discharged with the gap G constantly maintained to 0.04 to 0.05 millimeters, the sample momentarily becomes spherical and then is instantly pulled and adheres to the bottom of the reaction vessel. This prevents a conventional problem that the sample is brought back with the discharged sample remaining in spherical shape and adhering to the leading end of the sample probe. Since the leading end of the sample probe does not collide with the bottom of the reaction vessel, there is no risk of bending, breaking, and curling the leading end of the sample probe or damaging the bottom of the reaction vessel. Therefore, the outer diameter of the leading end of the sample probe can be manufactured as thinly as possible, thereby remarkably increasing the pipetting accuracy. When the sample probe is inserted into the sample in the sample vessel or when the sample probe discharges a sample into the reaction vessel, the fluctuation of the amount of sample adhering to the outside of the leading end of the sample probe can be reduced.

There are two different sample discharge methods: the "dummy method" with which the sample is suctioned more than necessary to leave dummy sample inside the probe and the "water extrusion method" with which all of the sample suctioned inside the sample probe is extruded with water from behind. When the amount of sample is 1 microliter or less, the "water extrusion method" is applied to extrude the sample with 5 microliters of water from behind, providing a favorable pipetting accuracy. The sample discharge method is not limited with the present invention. Further, a relation between the sample discharge start or stop timing and the timing at which the stepped portion abuts with the top edge of the reaction vessel is not limited with the present invention. (For example, starting sample discharge before the stepped portion abuts with the top edge of the reaction vessel is within the scope of the present invention. Further, completing sample discharge before the stepped portion abuts with the top edge of the reaction vessel is within the scope of the present invention.)

While only sample pipetting has specifically been explained with the present embodiment, the similar method can also be applied to reagent pipetting (very effective when a minute amount of reagent is pipetted), and the scope is not restricted by the type and use of the liquid to be pipetted.

What is claimed is:

1. An automated analyzer comprising:
   a reaction vessel;
   a liquid pipetting probe comprising:
      a first pipe for suctioning the liquid;
      a second pipe having a cylindrical shape which covers a portion of the first pipe from the outside; and
      an insulating material disposed between the first pipe and the second pipe,
   wherein the first pipe protrudes downward from the second pipe and the first pipe and the second pipe are bonded to each other and a length of the first pipe protruding from the second pipe is 0.04 - 0.05 millimeters shorter than a distance between a top edge of the reaction vessel and a bottom of the reaction vessel; and
   a probe drive unit which vertically moves the liquid pipetting probe to a height that the second pipe abuts with the top edge of the reaction vessel, and wherein an outer diameter of the second pipe is larger than an inner diameter of the reaction vessel.

2. The automated analyzer according to claim 1, wherein: the liquid pipetting probe is a sample pipetting probe.

3. The automated analyzer according to claim 1, wherein the first pipe and the second pipe are stainless steel pipes.

* * * * *